United States Patent
Larson et al.

(10) Patent No.: US 9,682,190 B2
(45) Date of Patent: Jun. 20, 2017

(54) RECIRCULATING COOLING SYSTEM FOR ENERGY DELIVERY DEVICE

(71) Applicant: Covidien LP, Mansfield, MA (US)

(72) Inventors: Eric W. Larson, Thornton, CO (US); Darion R. Peterson, Boulder, CO (US); Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 673 days.

(21) Appl. No.: 13/835,808

(22) Filed: Mar. 15, 2013

(65) Prior Publication Data

US 2014/0262201 A1   Sep. 18, 2014

(51) Int. Cl.
| | |
|---|---|
| *A61M 5/175* | (2006.01) |
| *A61M 5/168* | (2006.01) |
| *A61B 18/14* | (2006.01) |
| *A61F 7/00* | (2006.01) |
| *A61B 18/00* | (2006.01) |
| *A61B 18/18* | (2006.01) |
| *A61N 5/00* | (2006.01) |

(52) U.S. Cl.
CPC ....... *A61M 5/1689* (2013.01); *A61B 18/1492* (2013.01); *A61B 18/00* (2013.01); *A61B 18/1815* (2013.01); *A61B 2018/00023* (2013.01); *A61B 2018/00577* (2013.01); *A61F 2007/0054* (2013.01); *A61N 2005/005* (2013.01)

(58) Field of Classification Search
CPC ..................... A61F 2007/0054; A61M 5/1689
USPC ............................ 165/300; 607/104; 604/253
See application file for complete search history.

(56) References Cited

U.S. PATENT DOCUMENTS

| | | | | |
|---|---|---|---|---|
| 3,739,777 A | * | 6/1973 | Gregg ................ | A61M 5/1689 128/DIG. 13 |
| 3,832,998 A | * | 9/1974 | Gregg ................ | A61M 5/1689 128/DIG. 13 |
| 3,990,443 A | * | 11/1976 | Fletcher ............. | A61M 5/1689 128/DIG. 13 |
| 4,105,028 A | * | 8/1978 | Sadlier .............. | A61M 5/1689 128/DIG. 13 |

(Continued)

FOREIGN PATENT DOCUMENTS

| | | |
|---|---|---|
| CN | 203915069 U | 11/2014 |
| EP | 2 540 260 | 1/2013 |

(Continued)

OTHER PUBLICATIONS

U.S. Appl. No. 13/835,625, filed Mar. 15, 2013, Larson et al.

(Continued)

*Primary Examiner* — Devon Russell (57) ABSTRACT

A method for cooling a medical device includes fluidly connecting a cooling fluid reservoir to a medical device. The fluid connection includes a fluid out-flow path and a fluid return path corresponding to the fluid reservoir. The cooling fluid is pumped from the fluid reservoir to the medical device. The medical device is energized and the heat generated by the energization is absorbed by the cooling fluid pumped to the medical device. The cooling fluid is received at the reservoir containing the absorbed heat. The cooling fluid transfers the absorbed heat to the cooling fluid in the reservoir and to the environment adjacent to the reservoir.

8 Claims, 7 Drawing Sheets

(56) References Cited

U.S. PATENT DOCUMENTS

| | | | |
|---|---|---|---|
| 4,187,847 A * | 2/1980 | Loeser | A61M 5/16886 |
| | | | 128/DIG. 12 |
| 4,822,351 A * | 4/1989 | Purcell | A61J 1/2089 |
| | | | 141/291 |
| 5,049,129 A * | 9/1991 | Zdeb | A61M 5/1409 |
| | | | 141/309 |
| 5,304,130 A * | 4/1994 | Button | A61M 5/1409 |
| | | | 604/409 |
| 5,343,763 A * | 9/1994 | Nielsen | G01F 1/22 |
| | | | 73/861.55 |
| 5,411,052 A * | 5/1995 | Murray | A61M 5/1689 |
| | | | 137/392 |
| 5,545,161 A * | 8/1996 | Imran | A61B 18/1492 |
| | | | 606/41 |
| 5,733,319 A | 3/1998 | Neilson et al. | |
| 5,941,848 A * | 8/1999 | Nishimoto | A61M 5/1409 |
| | | | 604/82 |
| 6,036,680 A * | 3/2000 | Horne | A61M 5/162 |
| | | | 604/412 |
| 6,478,793 B1 | 11/2002 | Cosman et al. | |
| 6,506,189 B1 | 1/2003 | Rittman, III et al. | |
| 6,514,251 B1 | 2/2003 | Ni et al. | |
| 6,575,969 B1 | 6/2003 | Rittman, III et al. | |
| 6,679,865 B2 * | 1/2004 | Shekalim | A61M 5/16877 |
| | | | 604/246 |
| 7,052,463 B2 | 5/2006 | Peszynski et al. | |
| 7,425,208 B1 * | 9/2008 | Vitello | A61J 1/2096 |
| | | | 604/411 |
| 8,292,880 B2 | 10/2012 | Prakash et al. | |
| 8,308,726 B2 * | 11/2012 | Kumar | A61M 1/0058 |
| | | | 600/431 |
| 8,334,812 B2 | 12/2012 | Brannan | |
| 8,430,871 B2 | 4/2013 | Brannan | |
| 9,101,344 B2 | 8/2015 | Larson et al. | |
| 2004/0127840 A1 * | 7/2004 | Gara | A61M 1/3683 |
| | | | 604/4.01 |
| 2004/0267339 A1 * | 12/2004 | Yon | A61F 7/12 |
| | | | 607/105 |
| 2006/0031099 A1 * | 2/2006 | Vitello | A61M 5/14212 |
| | | | 705/2 |
| 2008/0051732 A1 * | 2/2008 | Chen | A61M 5/1689 |
| | | | 604/253 |
| 2009/0149930 A1 | 6/2009 | Schenck | |
| 2009/0222002 A1 | 9/2009 | Bonn et al. | |
| 2010/0053015 A1 | 3/2010 | Willyard | |
| 2010/0057074 A1 | 3/2010 | Roman et al. | |
| 2010/0228162 A1 | 9/2010 | Sliwa et al. | |
| 2011/0077637 A1 | 3/2011 | Brannan | |
| 2011/0118724 A1 * | 5/2011 | Turner | A61B 18/1815 |
| | | | 606/33 |
| 2011/0230753 A1 * | 9/2011 | Mahon | A61N 7/022 |
| | | | 600/411 |
| 2011/0295245 A1 | 12/2011 | Willyard et al. | |
| 2012/0323296 A1 * | 12/2012 | Takeda | A61F 7/10 |
| | | | 607/105 |
| 2013/0030426 A1 * | 1/2013 | Gallardo | A61B 18/1492 |
| | | | 606/33 |
| 2013/0237901 A1 * | 9/2013 | Woo | A61F 7/12 |
| | | | 604/24 |
| 2014/0081218 A1 * | 3/2014 | Winawer | A61M 5/168 |
| | | | 604/253 |
| 2014/0209486 A1 | 7/2014 | Chen | |
| 2014/0262201 A1 | 9/2014 | Larson et al. | |
| 2014/0281961 A1 | 9/2014 | Baker | |

FOREIGN PATENT DOCUMENTS

| | | |
|---|---|---|
| EP | 2540260 A1 | 1/2013 |
| EP | 2550924 A1 | 1/2013 |
| KR | 101016566 B1 | 2/2011 |
| WO | 2004034940 A1 | 4/2004 |
| WO | WO 2004/034940 | 4/2004 |
| WO | 2011056684 A2 | 5/2011 |
| WO | WO 2011/056684 | 5/2011 |

OTHER PUBLICATIONS

U.S. Appl. No. 13/838,805, filed Mar. 15, 2013, Baker.
U.S. Appl. No. 13/838,203, filed Mar. 15, 2013, Ladtkow et al.
European Search Report dated Oct. 1, 2014 issued in European Appln. No. 14 15 9833.
Partial European Search Report dated Jun. 3, 2014 issued in European Application No. 14159833.
European Search Report dated Oct. 1, 2014 issued in European Application No. 14159833.
Chinese Office Action dated Apr. 15, 2016, issued in Chinese Application No. 20140093847.9.
Chinese Office Action dated Oct. 17, 2016, issued in Chinese Application No. 201410093847.9.

* cited by examiner

RECIRCULATING COOLING SYSTEM FOR ENERGY DELIVERY DEVICE

BACKGROUND

1. Technical Field

The present disclosure relates to the use of energy delivery devices. More particularly, the present disclosure is directed to a method for cooling for energy delivery devices.

2. Background of the Related Art

Energy delivery procedures such as tissue ablation are used in numerous medical procedures to treat many conditions. Ablation can be performed to remove undesired tissue such as cancer cells. Ablation procedures may also involve the modification of the tissue without removal, such as to stop electrical propagation through the tissue in patients with an arrhythmia condition. Often the ablation is performed by passing energy, such as electrical energy, through one or more electrodes and causing the tissue in contact with the electrodes to heat up to an ablative temperature.

Electromagnetic (EM) ablation may also be used instead of direct energy discharge into tissue. For example, microwave (MW) ablation is a common example of such EM ablation where energy is applied to tissue through microwave radiation. EM ablation devices may require cooling to operate within desired parameters without damaging the ablation device or causing unintended tissue damage. Examples of EM ablation medical devices include percutaneous needle ablation probes and flexible intraluminal ablation catheters. Some devices implement cooling systems including a peristaltic pump that forces saline or another fluid through a tubing system operably connected to an energy delivery device. The saline solution draws heat from the energy delivery device and is then pumped out into a receptacle or to a drain. However, these systems require constant supply of saline bags, can be wasteful, and can be inefficient.

SUMMARY

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

According to aspects of the disclosure, a method of cooling a medical device is disclosed. The method includes providing a fluid reservoir, pumping a cooling fluid, and energizing a medical device. The method may also include providing a drip chamber, a fluid flow indicator, a tubing system, and/or an elbow. Pumping the cooling fluid may include pressurizing the cooling fluid before the fluid flow through the medical device. The method may also include measuring the temperature of the cooling fluid. In embodiments, a flow rate of fluid with the system is adjusted in response to the temperature of the cooling fluid.

According to other aspects of the disclosure, a method of recirculating a cooling fluid for use with an energy delivery device is disclosed. The method includes providing an energy delivery device and a recirculating cooling system connected to the energy delivery device. The recirculating cooling system is configured to maintain the energy delivery device with a desired temperature range. The recirculating cooling system may include a tubing system and a fluid reservoir. The tubing system configured to interconnect the fluid reservoir with the energy delivery device and carry the cooling fluid from the fluid reservoir and through the energy delivery device before returning the cooling fluid to the fluid reservoir. The method may further include providing a thermocouple on a portion of the cooling system to measure a system temperature. The desired temperature range may include an upper limit. The flow rate of the fluid may be increased with the system temperature approaches the upper limit.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, the disclosed embodiments are merely examples of the disclosure and may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with at least one aspect of the present disclosure, an energy delivery device cooling system is disclosed. Referring generally to FIGS. 1-6, the system 1000 includes a reservoir connector assembly 100 in communication with a reservoir 200. The reservoir 200 is configured to contain or hold a cooling fluid. The reservoir connector assembly 100 may include an elongate member 101 configured to extend into the reservoir 200. Tubing system 400 connects the reservoir 200 with a medical device having inlet and outlet ports and forming a closed loop cooling system 1000, as will be described in greater detail below. Examples of medical devices to which the system 1000 may be connected can be found in commonly owned U.S. Pat. No. 8,334,812, U.S. patent application Ser. No. 12/607,221, filed Oct. 28, 2009, and now published as U.S. Patent Application No. 2011/0098696, U.S. patent application Ser. No. 13/838,805, filed Mar. 15, 2013, and now published as U.S. Patent Publication No. 2014/0281961, and U.S. patent application Ser. No. 13/836,203, filed Mar. 15, 2013, and now published as U.S. Patent Publication No. 2014/0046315, each of which is incorporated herein by reference in its entirety.

In some embodiments, the elongate member 101 can have any length and shape capable of being inserted into the reservoir 200. For example, the elongate member 101 can be a spike with a penetrating tip. In other embodiments, the elongate member 101 can have a blunt or substantially flat tip. The elongate member 101 can be substantially cylindrical, and in the embodiments with a piercing tip, the tip can be symmetrically conical or non-symmetrically conical.

Figure 1:
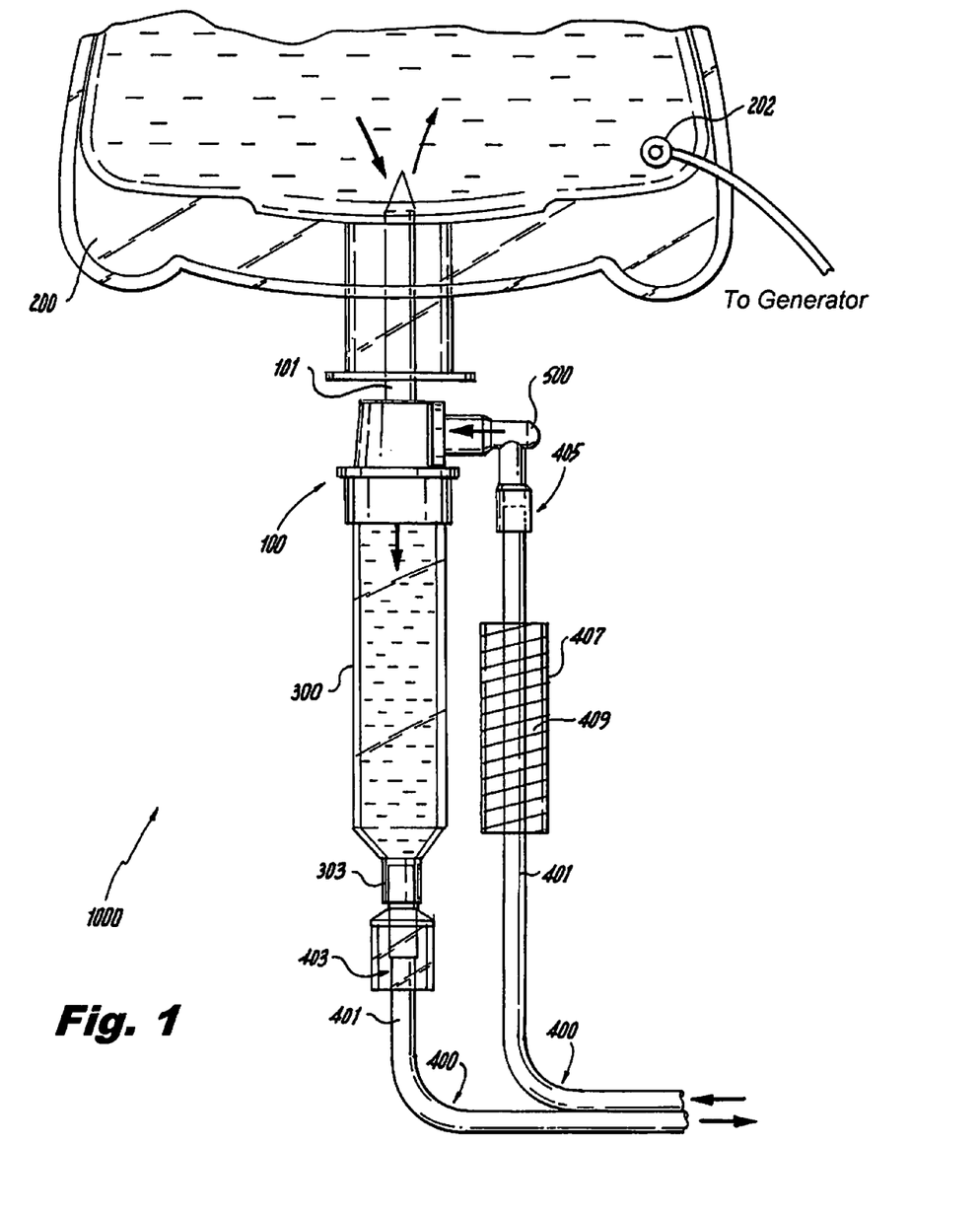
FIG. 1 is a side view of a portion of a cooling system in accordance with the present disclosure.
Figure 2:
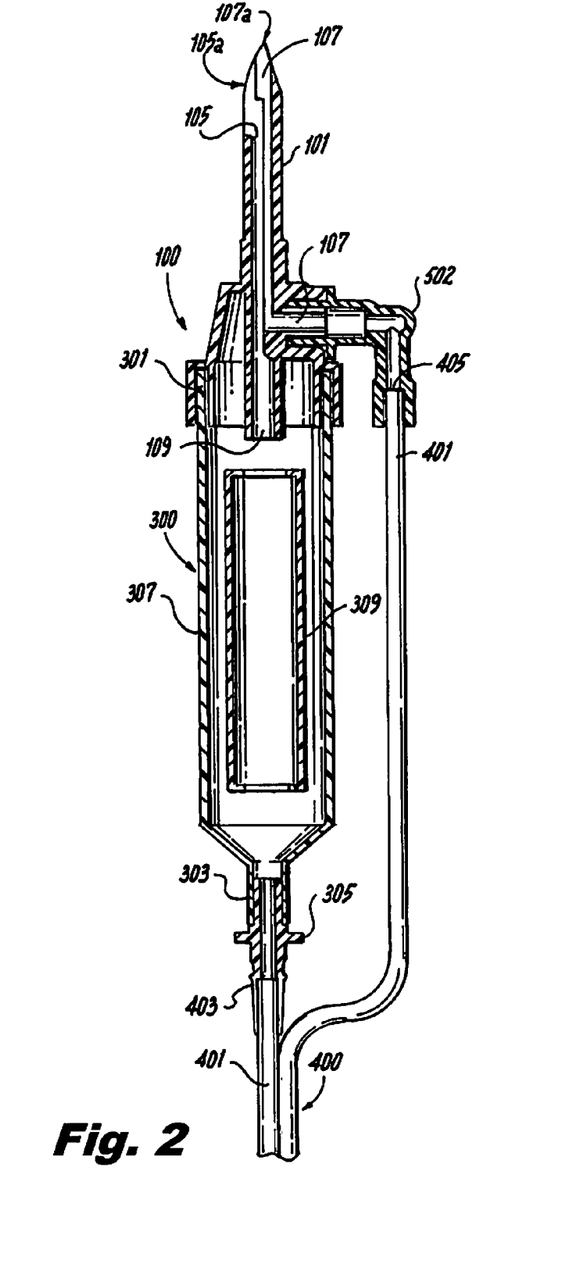
FIG. 2 is a cross-sectional view of a drip chamber and flow indicator, in accordance with the present disclosure.

Referring specifically to FIG. 2, the elongate member 101 has at least a first lumen 105 and a second lumen 107 defined therethrough. Each lumen 105, 107 is configured to be in fluid communication with the reservoir 200 shown in FIG. 1 at openings 105a and 107a respectively. The first lumen 105 may act as an inflow lumen for drawing fluid from the reservoir 200 and the second lumen 107 may act as a return lumen for returning fluid to the reservoir 200.

Lumens 105, 107 and openings 105a, 107a may have the same or different diameters. The diameter of the lumens 105, 107 may be selected based on a desired volumetric flow rate and fluid velocity for a given medical device. For example, to promote mixing in the reservoir 200, a smaller diameter lumen 107 can be chosen to achieve a higher velocity of the fluid for a given pressure. The increased velocity can increase turbulent flow within the reservoir 200 and/or the tubing system 400, resulting in increased mixing of the fluid. This increased mixing can promote homogenization of the fluid temperature within the reservoir 200 and/or the tubing system 400. The turbulent flow can also increase the efficiency of the transfer of heat from the fluid to the surrounding environment.

At least one outflow port 109 is in fluid communication with the first lumen 105 and allows fluid to flow from the reservoir 200 into a drip chamber 300 or directly into the tubing system 400. With continued reference to FIG. 2 and added reference to FIG. 4A, the reservoir connector assembly 100 includes a return port 103 configured to allow cooling fluid to return to the reservoir connector assembly 100 from the tubing system 400. The return port 103 is in fluid communication with the second lumen 107 and may be configured to allow for direct or indirect fluid communication with tubing system 400. It is also envisioned that the reservoir connector assembly 100 includes more than one return port 103.

In some embodiments, the elongate member 101 further includes a third lumen and a fourth lumen having third and fourth openings, respectively, and in fluid communication with the reservoir 200 and the outflow port 109. Similarly, added lumens may also connect to the return port 103.

Figure 8:
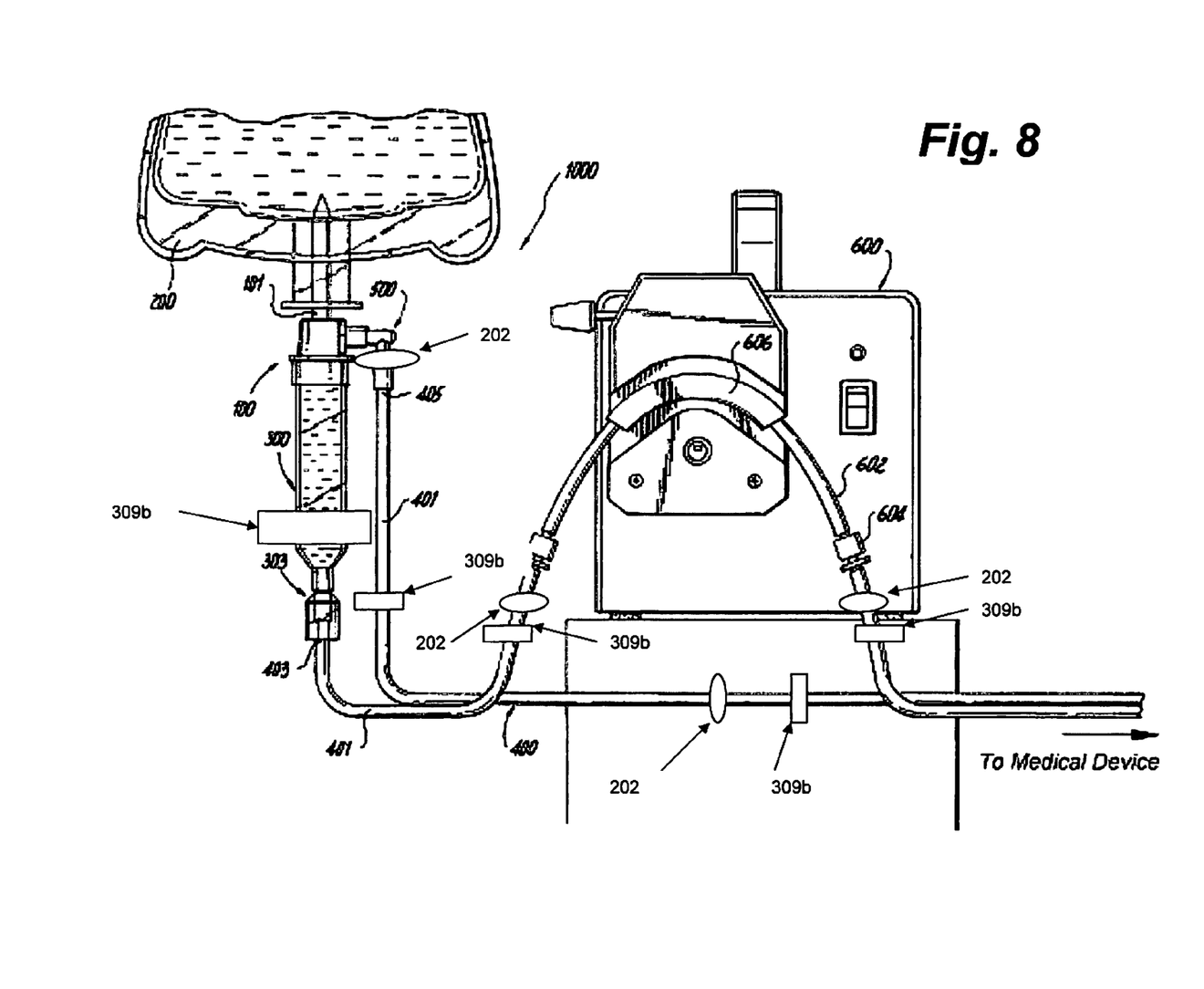
FIG. 8 is a side view of a cooling system in accordance with the present disclosure depicting locations of flow sensors and thermocouples.

The elongate member 101 or the reservoir 200 may include a thermocouple 202 operably connected thereto to monitor a temperature of the fluid inside the reservoir 200. Alternatively, the thermocouple 202 may be placed in various locations to measure the temperature of the fluid in the system 1000, as shown in FIG. 8. For example, the thermocouple 202 may be placed near the opening of the second lumen 107 to measure the temperature of the fluid flowing into the reservoir 200, near the first lumen 105 to measure the temperature of the fluid flowing out of the reservoir 200, in a portion of the tubing system 400 to measure the temperature of fluid flowing therein, or any combination thereof. The thermocouple 202 may be connected to an energy source for the medical device, for example a microwave generator (not shown), and may be employed as a safety shut off for the energy source such that if the temperature of the fluid rises beyond a set threshold that indicates insufficient cooling, the energy source is shut off to prevent undesired damage to patient tissue during treatment.

As shown in FIG. 1, a reservoir connector assembly 100 fluidly connects the reservoir 200 with a drip chamber 300. The drip chamber 300 may include a top portion 301 (FIG. 4A) configured to receive a portion of the reservoir connector assembly 100 and a bottom portion 303 configured to connect the drip chamber 300 in fluid communication with the tubing system 400. In embodiments, a fluid connector 305 connects the bottom portion 303 with the tubing system 400 and facilitates fluid communication therebetween. Between the top portion 301 and the bottom portion 303 is a central portion 307, which may be formed as a cylinder. As shown in FIGS. 2, 7, and 8, the central portion 307 of the drip chamber 300 may also include a flow indicator 309 for indicating that a fluid is flowing from the reservoir 200 through the drip chamber 300 to the tubing system 400.

Figure 3:
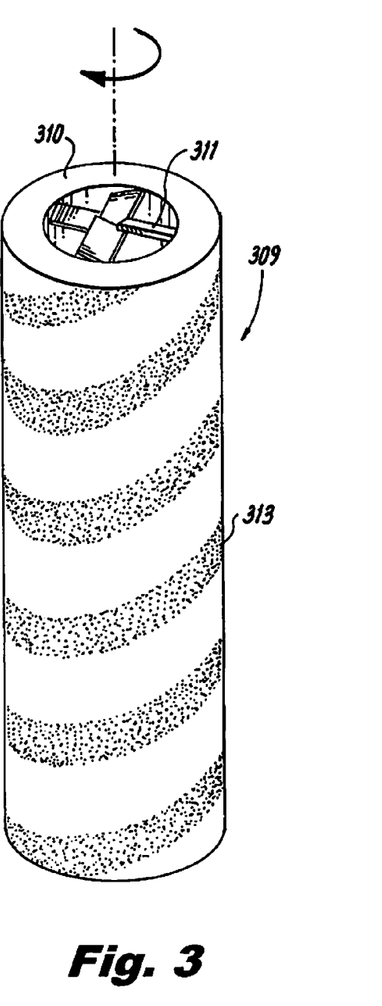
FIG. 3 is a perspective view of a flow indicator of a cooling system in accordance with the present disclosure.

As shown in FIG. 3, the flow indicator 309 may be formed of a hollow cylinder 310 with hydrofoils 311 configured to rotate the hollow cylinder 310 in the drip chamber 300 when fluid flows through the flow indicator 309. The flow indicator 309 may include a design 313 disposed on an outer surface thereof that visually indicates that the cylinder 309 is rotating, and thus that fluid is flowing therethrough. For example, the design 313 may resemble a barber-shop pole, however, other designs can be used to indicate fluid flow, for example a corporate logo COVIDIEN® or other graphic design. The cylinder 310 may be formed of a material with a specific gravity causing the cylinder 310 to either be neutrally buoyant in the cooling fluid or to float in the cooling fluid. Other embodiments of flow indicators 309 may be utilized that are suitable for indicating flow in the drip chamber 300 including but not limited to low density balls, floating material indicators, paddle wheel indicators, or the like.

Figure 7A:
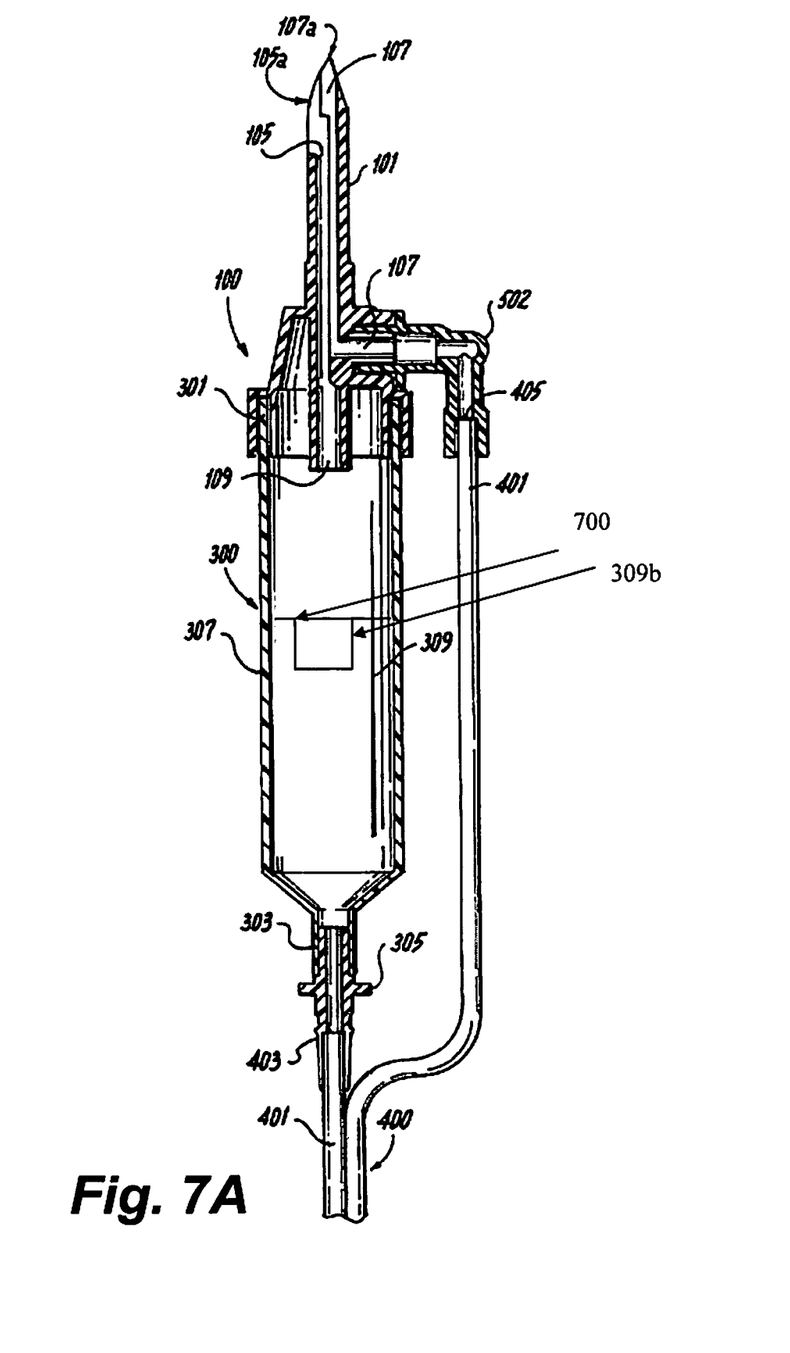
FIGS. 7A and 7B are cross-sectional views of a drip chamber and a flow indicator, in accordance with the present disclosure.
Figure 7B:
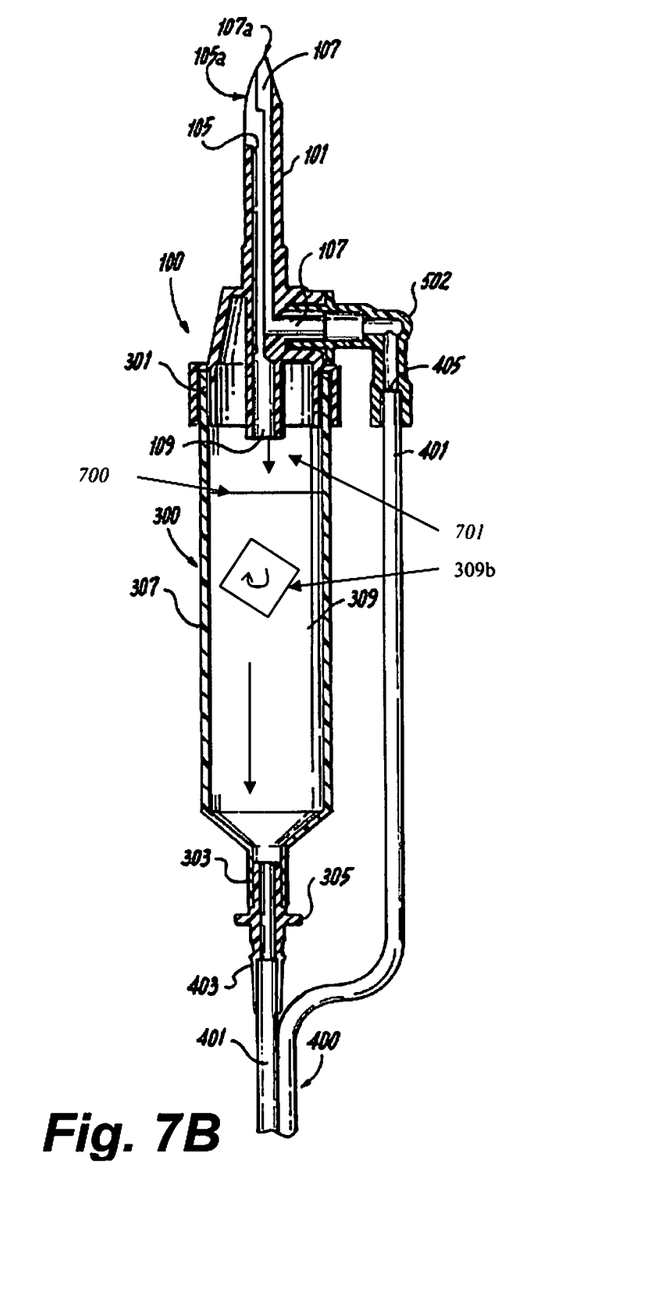

An alternative arrangement of a flow indicator 309a is depicted in FIGS. 7A and 7B. As shown in FIGS. 7A and 7B, the flow indicator 309a is generally in the shape of a cube, though other geometric shapes may be employed without departing from the scope of the present disclosure. The cube shape may be advantageous by eliminating the possibility of the flow indicator 309a occluding the bottom portion 303 of the drip chamber 300 when the system 1000 is initially primed with the fluid. The flow indicator 309a has a density related to the cooling fluid such that when fluid is not flowing through the drip container 300 the flow indicator 309a floats to the upper surface 700 of the fluid in the drip container 300 as shown in FIG. 7A and when fluid is flowing through the drip container 300 the flow indicator 309a partially submerges beneath the surface 700 and may also rotate to provide visual indicia of fluid flow as shown in FIG. 7B.

The tubing system 400 may include one or more return fluid flow indicators disposed thereon to indicate that a fluid is returning from the medical device to the reservoir 200 through tubing system 400. Examples of such return flow indicator include bubble indicators and traps, Venturi-style indicators, Hall-effect fluid flow indicators, and the like. Indicators, such as bubble indicators and venturi devices, also have the dual purpose of removing any gas which may have entered the system or vapor from the liquid flow to prevent disruption in the flow. Other fluid flow indicators may also be employed to measure fluid velocity, pressure, or volumetric flow rate. Examples of the fluid flow indicators are currently sold by Introtek International under the name BDC and BER Ultrasonic Clamp-on Air Bubble, Air-in-line & Liquid level Detection Systems as well as the Drip Chamber Ultrasonic Liquid Level Sensors.

FIG. 8 illustrates numerous locations where flow indicators 309b and thermocouples 202, as described above, may be employed within system 1000. The flow indicators 309b are flow sensors that detect flow of a fluid between portions of the flow indicators 309b. The flow indicators 309b and thermocouples 202 may be attached to various portions of the system 1000 and may be attached to devices (not shown) that provide audible and/or visual indicia of fluid flow within the system 1000. Further, the devices themselves may provide audible and/or visual indicia when fluid is not flowing within portions of the system 1000, e.g. when a tube is kinked or blocked.

Referring now to FIGS. 1 and 2, the tubing system 400 includes one or more tubes 401 that allow a fluid to flow from the reservoir connector assembly 100, through an energy delivery device (not shown) such as an ablation needle or catheter or an energy source, and back to the reservoir connector assembly 100. The tubing system 400 may include a first end 403 and a second end 405.

In the illustrated embodiment, the first end 403 is in fluid communication with the outflow port 109, either indirectly through the bottom portion 303 of drip chamber 300 or by direct connection to outflow port 109, and is configured to allow fluid to flow into tubing system 400. The second end 405 is in fluid communication with the return port 103, and is configured to allow fluid to return to the reservoir 200 through the second lumen 107.

Tubing system 400 may also include one or more thermal diffusion devices 407 configured to draw heat from the fluid and diffuse the heat to the ambient environment. As shown in FIG. 1, the thermal diffusion device 407 includes a series of fins 409 in contact with the tube 401 returning from a medical device. A fan may be employed to direct airflow over the fins and increase the cooling effect. While shown connected to the tube 401, a thermal diffusion device 409 could also or alternatively be employed on the reservoir 200. A further alternative could employ passing the tube 401 returning from the medical device through a reservoir containing cold water or ice water in order to further draw heat out of the fluid flowing through the tubes 401.

Figure 5A:
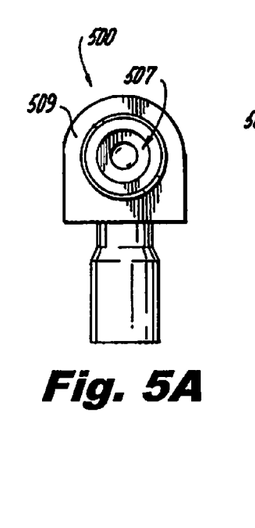
FIG. 5A is a cross-sectional view of a fluid return elbow member in accordance with the present disclosure.
Figure 5B:
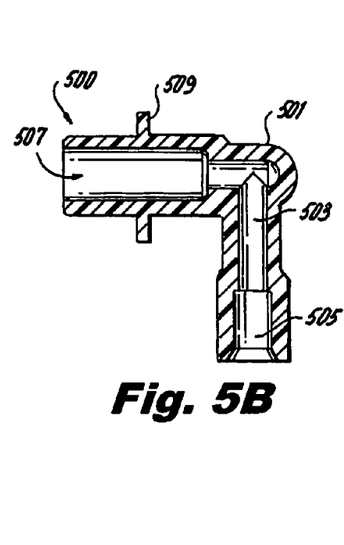
FIG. 5B is a front view of the fluid return elbow of FIG. 5A.
Figure 5C:
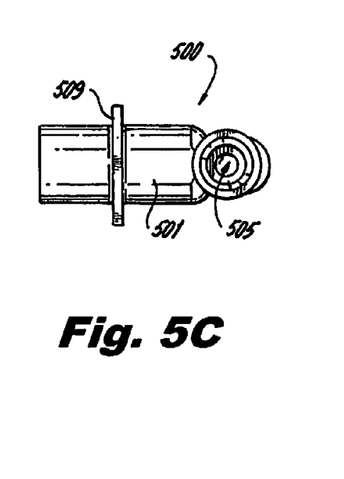
FIG. 5C is a bottom view of the fluid return elbow of FIG. 5A.

The system 1000 may further include an elbow member 500 connected to the second end 405 of the tubing system 400 as shown in FIGS. 5A-C. The second end 405 of the tubing system 400 in fluid communication with the return port 103 through the elbow member 500.

The elbow member 500 may include a body 501 defining a lumen 503, an inflow port 505 in fluid communication with the lumen 503, and an outflow port 507 in fluid communication with the lumen 503. The inflow port 505 is configured to connect to a return section or second end 405 of a tubing system 400, and the outflow port 507 is configured to connect to or accept the return port 103 of the reservoir connection assembly 100.

Figure 4A:
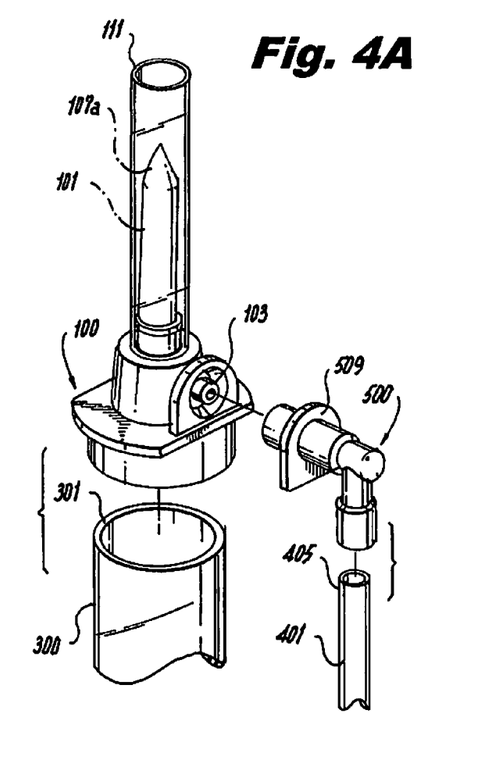
FIG. 4A is an exploded view of a portion of the cooling system in accordance with the present disclosure.
Figure 4B:
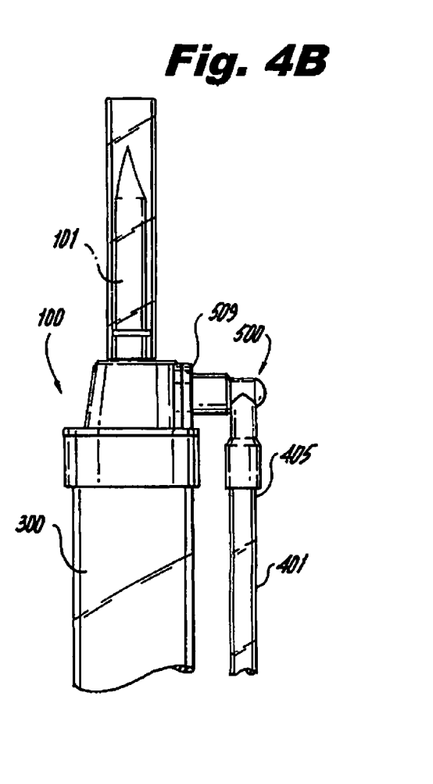
FIG. 4B is a side view of the portion of the cooling system of FIG. 4A.

The elbow member 500 may further have a flange 509 disposed around the outflow port 507 to ensure proper alignment of the elbow 500 with the reservoir connection assembly 100 as shown in FIGS. 4A and 4B. For example, as shown, flange 509 has a tombstone shape with a flat portion on a bottom portion thereof to allowing for connection with return port 103 in only one orientation of the elbow 500.

In at least some embodiments, the elbow 500 is formed of molded plastic. The elbow 500 may be injection molded, blow molded, or formed in any other suitable manner known in the art. The elbow 500 may be made of one solid piece or a conglomeration of subparts.

Figure 6:
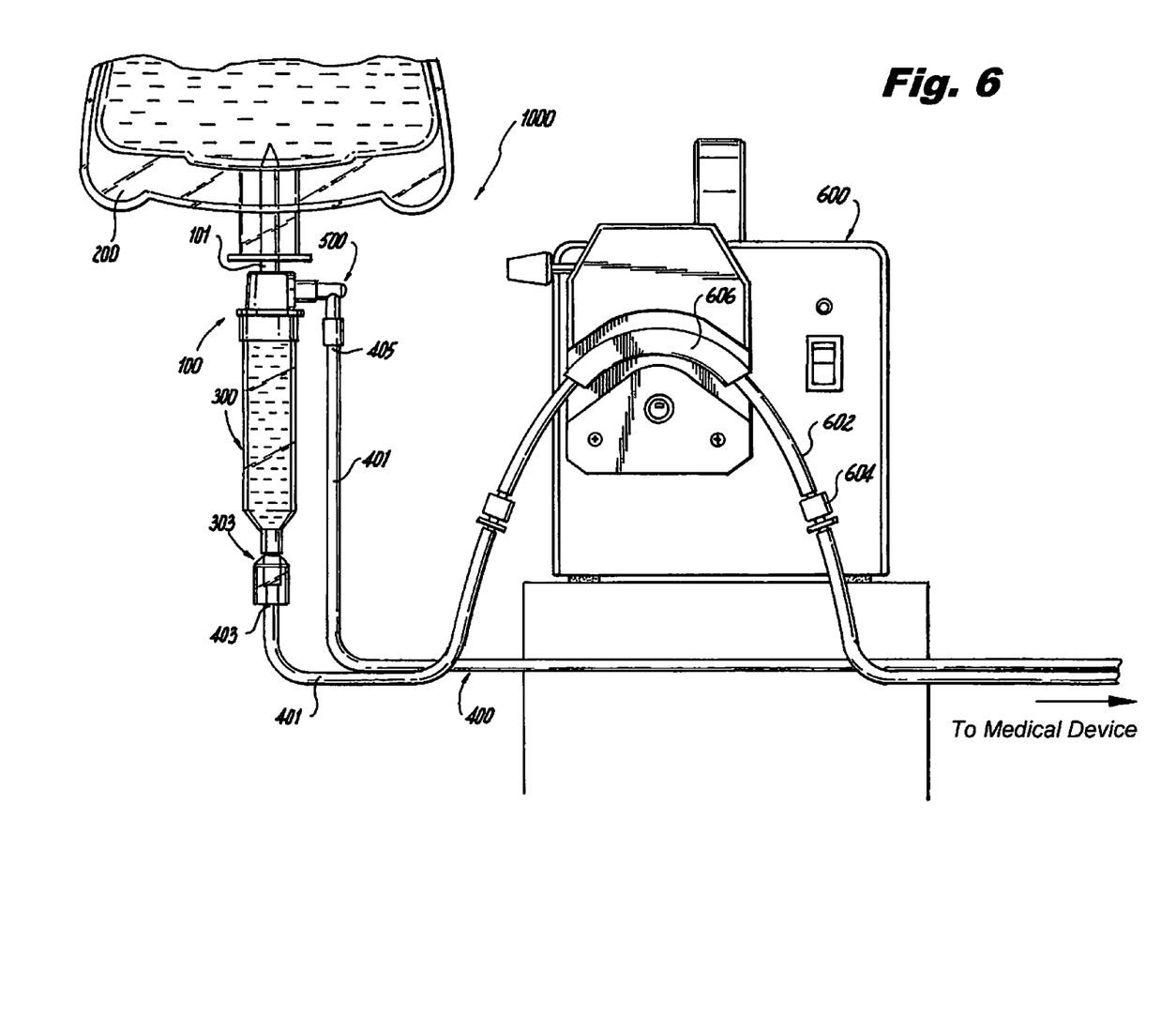
FIG. 6 is a side view of a cooling system in accordance with the present disclosure.

In one embodiment, one or more pumps may be used to control fluid flow through the cooling system 1000. Referring to FIG. 6, a pump 600 may be connected to the tubing system 400 to pressurize a fluid in the tubing 401. While any pump known in the art can be used, as shown FIG. 6, the type of pump 600 used is a peristaltic pump which applies pressure to compress the outside of a pump tubing 602 forcing fluid downstream towards the medical device. The pump tubing 602 may be made of a thicker gauge of the same material or a different material than the tubing 401, thus allowing it to withstand the repetitive stresses of the peristaltic pump for the duration of a medical procedure. Connectors 604 may be used to fluidly connect the pump tubing 602 to the tubing 401. Further, a protective slip cover 606 may alternatively be used to protect either the pump tubing 602, or the tubing 401, if no pump tubing 602 is utilized. Though described herein with respect to a peristaltic pump, any device suitable to create a pressure to advance fluid through the tubing 401 in the cooling system 1000 may be used.

As an alternative to using a peristaltic pump 600, the entire system 1000 may rely on gravity and the change in density of the fluid as it is heated to allow the fluid to circulate through the system 1000. For example, as water heats, its density at 1 atm (sea level) decreases from about 62.4 lb/ft$^3$ at 60° F. to about 60 lb/ft$^3$ at 212° F. This difference in density may in some circumstances promote sufficient circulation of the fluid through the system 1000 to maintain proper cooling of the medical device.

The fluid used in cooling system 1000 may be any suitable liquid such as saline solution, de-ionized water, sugar water, and combinations thereof, or the like. For example, the reservoir 200 may be a saline bag traditionally used in medicine.

In use, the tubing system 400 is connected to a medical device (not shown) to cool the medical device. The medical device may have cooling lumens such as those found in microwave ablation probes and microwave ablation catheters. The tubing system 400 connects to an inflow port of the medical device allowing cooling fluid to flow through the lumens of the medical device to and flow out of an outflow port on the medical device. The cooling fluid may pumped from the reservoir 200 through the medical device, as described above, or alternatively, the cooling fluid may be gravity fed to the medical device. The cooling system 1000 may include the reservoir connection assembly 100 and the drip chamber 300 in fluid communication with the tubing system 400, as described above. The cooling fluid flows from the reservoir 200 through the reservoir connection assembly 100, drip chamber 300, and the tubing system 400 into the inflow port of the medical device. The fluid returns to the reservoir 200 flowing from the outflow port of the medical device through tubing system 400, the return port 103, and the second lumen 107 of reservoir connection assembly 100. The fluid extracts or absorbs heat from the medical device to cool the device. As the fluid is traveling through system 1000, it releases some heat into the environment surrounding the tubing system 400. If thermal diffusion devices 407 are connected to the system 1000, heat may be released from the fluid more efficiently, allowing for a reduced operating temperature of the system 1000.

Temperatures maintained in the system 1000 and the energy delivery device should be within a range to avoid injury to the patient and adequate to allow flow through the system. For example, the temperature should be below approximately 113° F. to avoid injury to the patient and above the freezing temperature of the fluid. Pressures and flow rates within the system 1000 and the components thereof may be varied through variations in pump speed, and through design of the system 1000 and the components thereof.

Some example performance parameters include:

|  | Pump | Microwave Needle Ablation Probe | Microwave Ablation Catheter |
| --- | --- | --- | --- |
| Pressure | 35-45 psi Up to 60 psi | 45-55 psi | 50-70 psi |
| Flow Rate | 4.8-6.1 in$^3$/min | 4.2-5.5 in$^3$/min | 1.4-1.8 in$^3$/min |

One of the advantages of the cooling system 1000 described herein is that it can employ standard sterile saline bags as the fluid reservoir, which eliminates the need for a specialized fluid source. Further the system 1000 recirculates fluid as opposed to simply dumping the cooling fluid after one pass through the medical device, thereby conserving cooling fluid and eliminating the need for a collection bucket or bag.

Methods are also disclosed herein. In an embodiment, a method may include providing a saline bag or other fluid reservoir and a saline bag elongate member having multiple lumens defined therein. The saline bag elongate member includes at least one return port connected to at least one of the lumens. The method may also include providing a drip container such as the drip container 300 disclosed herein.

The method may further include providing an elbow 500 as disclosed herein. The method further includes connecting the elbow 500 to the return port of the saline bag elongate member to allow fluid flow to return into the saline bag through the return port. The method also includes the step of connecting a return portion of the tubing system 400 to the elbow 500.

Also disclosed is a method for recirculating a cooling fluid for use with an energy delivery device. The method includes providing an energy delivery device, providing a recirculating cooling system connected to the energy delivery device, and recirculating a fluid through the cooling system and energy delivery device to maintain the energy delivery device at a desired temperature or within a desired temperature range to prevent undesired damage to tissue. The desired temperature range may include an upper limit corresponding to a temperature above which tissue is damaged and a lower limit below which the fluid will not flow within the system. The flow rate of fluid within the system may be adjusted as the temperature approaches the upper limit or the lower limit. For example, when the temperature approaches the upper limit the flow rate may be increased to increase the cooling of the medical device. The system may include visual or audible indicia when the temperature approaches the upper or lower limit.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figs. are presented only to demonstrate certain examples of the disclosure. Other elements, steps, methods, and techniques that are insubstantially different from those described above and/or in the appended claims are also intended to be within the scope of the disclosure.

What is claimed is:

1. A method of cooling a medical device comprising:
fluidly connecting a fluid reservoir to a medical device, wherein the fluid connection includes a fluid out-flow path and a fluid return path;
pumping the cooling fluid from the fluid reservoir to the medical device with a pump;
providing local indicia of cooling fluid flowing from the fluid reservoir to the pump by observing movement of a spinning member positioned within a drip chamber, the spinning member configured to spin about a longitudinal axis of the drip chamber defined by a flow path of the cooling fluid through the drip chamber, wherein the spinning member is a hollow cylinder disposed about the longitudinal axis;
energizing the medical device;
receiving at the fluid reservoir the cooling fluid containing absorbed heat from the energized medical device; and
transferring the absorbed heat to the cooling fluid in the fluid reservoir.

2. The method of claim 1, wherein the step of pumping includes providing a pump in fluid communication with the fluid reservoir, the pump pressurizing the cooling fluid for delivery to the medical device.

3. The method of claim 1, further comprising measuring the temperature of the cooling fluid within at least one of the fluid reservoir, the tubing system, or the medical device.

4. The method of claim 3, further comprising increasing or decreasing a flow rate of the cooling fluid in response to the temperature of the cooling fluid.

5. The method of claim 1, wherein the fluid reservoir is a saline bag and the cooling fluid is saline.

6. The method of claim 1, wherein the fluid reservoir is fluidly connected to the medical device via a tubing system.

7. The method of claim 1, wherein fluidly connecting the fluid reservoir to the medical device includes inserting an elongate member, that defines the fluid out-flow path and the fluid return path, into a main volume of the fluid reservoir such that the fluid out-flow and return paths of the elongate member have openings within the main volume of the fluid reservoir.

8. The method of claim 1, wherein providing local indicia of cooling fluid flowing from the fluid reservoir to the pump by observing movement of the spinning member positioned within the drip chamber includes cooling fluid contacting hydrofoils of the spinning member disposed within the hollow cylinder of the spinning member.

* * * * *